United States Patent [19]

Herbison

[11] Patent Number: 4,741,697
[45] Date of Patent: May 3, 1988

[54] CHAIRSIDE FILTER/DRYER FOR DENTAL AIR SYRINGE

[76] Inventor: Richard J. Herbison, 198 Park Rd., Pittsford, N.Y. 14534

[21] Appl. No.: 945,826

[22] Filed: Dec. 24, 1986

[51] Int. Cl.⁴ .................. A61C 3/00; B01D 39/00; B01D 19/00
[52] U.S. Cl. ......................... 433/25; 55/387; 55/274
[58] Field of Search .............. 433/80, 81, 82, 25, 433/27; 55/274, 316, 487, 485, 387, 323

[56] References Cited

U.S. PATENT DOCUMENTS

| | | | |
|---|---|---|---|
| 2,029,734 | 2/1936 | Meitzler | 433/80 |
| 3,279,151 | 10/1966 | Kaver, Jr. et al. | 55/26 |
| 3,347,387 | 10/1967 | Balogh | 55/316 |
| 3,348,692 | 10/1967 | Balogh | 55/316 |
| 3,401,691 | 9/1968 | Beu | 433/80 |
| 3,494,110 | 2/1970 | Reed et al. | 55/316 |
| 3,681,899 | 8/1972 | Grote | 55/387 |
| 3,841,484 | 10/1974 | Domnick | 55/274 |
| 3,891,417 | 6/1975 | Wade | 55/274 |
| 4,015,959 | 4/1977 | Grote | 55/274 |
| 4,487,618 | 12/1984 | Mann | 55/323 |

Primary Examiner—John J. Wilson
Assistant Examiner—Rohini H. Sarma
Attorney, Agent, or Firm—Shlesinger, Fitzsimmons, Shlesinger

[57] ABSTRACT

The cartridge has a transparent housing with nipples at opposite ends thereof releasably insertable in the flexible tube which supplies compressed air from a primary filtering mechanism to a dental air syringe. The cartridge contains a filter element which changes color as it removes a predetermined residual contaminate from the compressed air. The cartridge is positioned adjacent the dental chair so the dentist may observe the change of color in the filter element.

11 Claims, 2 Drawing Sheets

CHAIRSIDE FILTER/DRYER FOR DENTAL AIR SYRINGE

BACKGROUND OF THE INVENTION

This invention relates to dental air syringes, and more particularly to a replaceable filter cartridge which is releasably insertable into a compressed air supply line adjacent to a dental air syringe, both to remove residual fluids and/or particles from the air, and to provide visible means for determining when the cartridge need be replaced.

Dentists have long employed compressed air for drying tooth surfaces during the execution of a variety of dental procedures. Typically a fine jet of compressed air is directed into the mouth of a patient through the nozzle portion of a small, hand-held dental syringe. At its end remote from its nozzle the syringe usually is connected to a compressed air supply by a flexible tube, which permits the dentist or his assistant to manipulate the syringe manually.

One of the major problems of dental air syringe systems of the type currently employed is the need for removing moisture and oil from the air before it is delivered to the patient's mouth. For example, current research has developed a variety of dental materials that rely upon a critical "bonding" of the material to tooth dentin or enamel. During procedures utilizing such materials the dentin or enamel first must be chemically treated to produce a clean, reactive surface, after which the surface is washed with water and air dryed before applying to the surface the particular material which is to be used for covering or rebuilding the tooth surface. It is essential that the air, which is used for drying, be completely free from moisture and oil to prevent contamination of the reactive surface. If water or oil is present in even the smallest amount, it will prevent proper bonding between the treated surface and the material which is being applied to the tooth dentin or enamel.

Heretofore it has been customary to use rather sophisticated compressed air dehydration systems for supplying dry air to dental syringes of the type described above. U.S. Pat. No. 3,279,151 for example, discloses a system in which compressed air passes through a chamber containing a desiccant which is designed to remove moisture from the air before it reaches the associated instrument. The system is adapted periodically to reverse the flow of air through the desiccant chamber, while at the same time heating the chamber to vaporize the moisture in the desiccant The moisture is then exhausted by the reversed air flow to atmosphere, thus restoring the desiccant so that it can once again be utilized for absorbing air.

The problem with this type of system is that, while it removes most of the moisture from the air, nevertheless residual amounts of moisture do in fact remain in the air after it leaves the desiccant chamber on its way to the dental syringe. In fact moisture laden air bypasses the desiccant chamber for 30 minutes during the heating cycle when the apparatus is first turned on. Moreover, the presence of the residual moisture and/or oil, in the air remains unknown to the dentist, who assumes the air to be dry, and therefore is unaware that moisture in the air may in fact have contaminated the reactive surface of the dentin or enamel.

U.S Pat. No. 4,487,618 discloses a rather sophisticated, heatless dehydration system using an in-line trap for removing water and/or oil vapor from a compressed air line. Although this system suggests using removable filter cartridges, the apparatus appears to have been designed for heavy machinery, and the patent was not at all concerned with the complete removal of moisture and oils for purposes of dental treatment.

In any case, these heatless or heat cycled type desiccant apparatus need to have the desiccant replaced periodically, but there is no way for the average dentist to know when such replacement is necessary. More importantly, since most such systems are well out of view of the dentist, the dentist or other operator has no way of knowing at any given instant whether or not the dehydrating system is properly functioning, and therefore may be unaware that a treated surface has become contaminated because of a failure in the filtering apparatus.

Furthermore, depending on the type of dental procedure employed it may be desirable, such as for example if oral surgery is involved, to remove even the smallest of particulate matter from the compressed air before applying it to the site of the wound or incision.

It is an object of this invention, therefore, to provide for dental air syringes of the type described a novel filter cartridge which is disposed to be releasably mounted in the compressed air supply line of the syringe to remove residual moisture and/or oil from the air.

It is another object of this invention to provide an improved cartridge of the type described which is adapted to be positioned in the compressed air supply line of a syringe in such a manner that one or more filter elements in the cartridge are readily observable by the dentist, and are designed to undergo a change in color when saturated or clogged, thereby to provide a visible indication of when the elements need be replaced.

Other objects of the invention will be apparent hereinafter from the specification and from the recital of the appended claims, particularly when read in conjunction with the accompanying drawings.

SUMMARY OF THE INVENTION

A sleeve containing an indicating desiccant, and/or a treated filter element for removing oil, is sealed at opposite ends by a pair of end caps, each of which has a tubular nipple projecting from its closed end for use in releasably connecting the sleeve in the compressed air supply line of a dental syringe. The sleeve, which is transparent, is mounted in the supply line adjacent the syringe so that it is readily observable by the dentist. As the desiccant absorbs moisture its color changes from one color to another, for example from blue to pink, thus informing the dentist that residual moisture in the air is in fact being filtered out from the air, and indicating also when the desiccant should be replaced.

In the case of the treated, oil-removing filter element, it also changes from one to another color, for instance from pink to red, as it filters oil out from the compressed air supply, thus providing a visual indication of its efficacy in removing oil, and providing a visible warning when it should be replaced.

In another embodiment the sleeve contains a plurality of axially spaced dye capsules, each of which is sandwiched in the bore of the sleeve between a stationary screen element and an axially movable or flexible membrane filter designed to remove particulate matter from compressed air as it passes axially through the sleeve. Each stationary screen is positioned down stream of the air so that as each membrane becomes plugged or clogged it exerts progressively more axial pressure on the adjacent capsule until the latter ruptures. Each capsule contains a differently colored dye, so that when it ruptures it indicates visually which membrane has become clogged. This cartridge is particularly suitable for supplying compressed air free of microbiological contaminates.

THE DRAWINGS

DETAILED DESCRIPTION OF THE PREFERRED EMBODIMENTS

Figure 1:
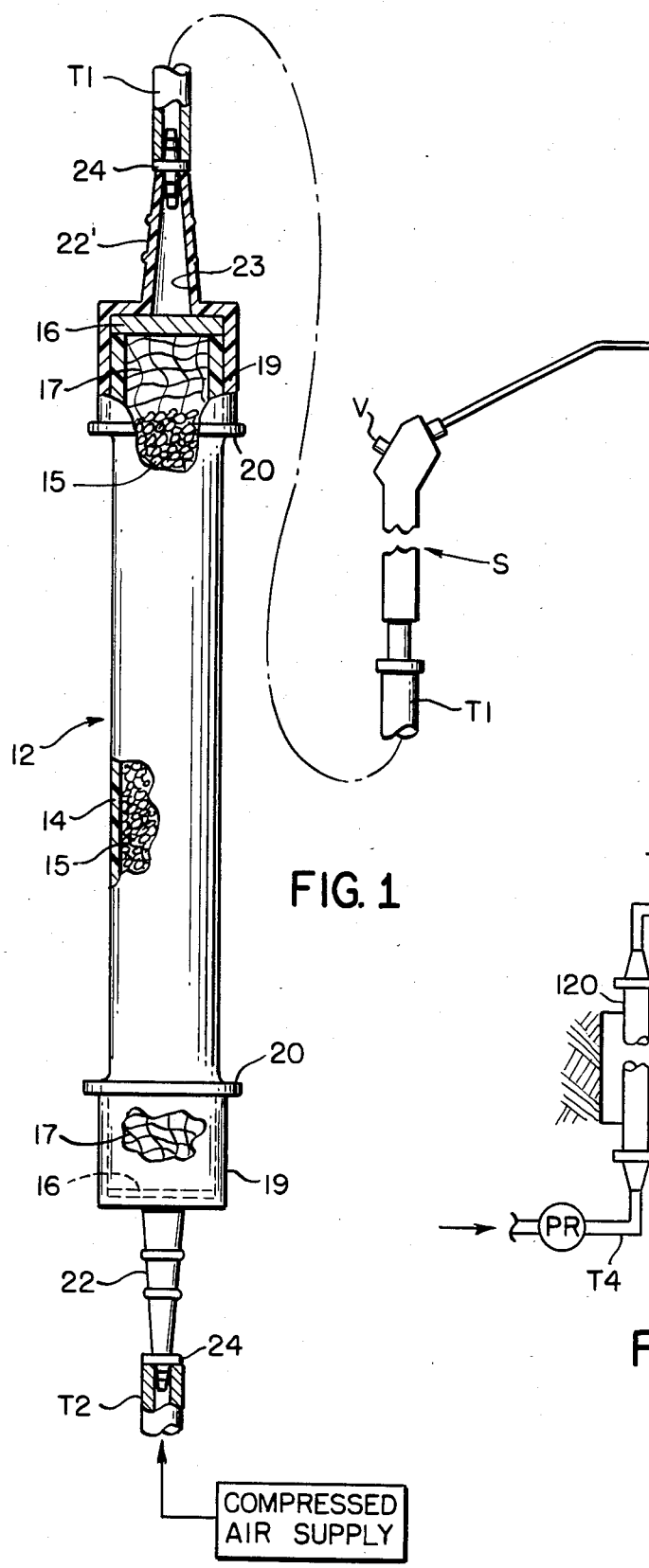
FIG. 1 is a fragmentary side elevational view of a dental syringe and a novel filter cartridge therefor made according to one embodiment of this invention, the cartridge being shown connected in the compressed air supply line for the syringe, and having parts thereof broken away and shown in section.

Referring now to the drawings by numerals of reference, and first to the embodiment shown in FIG. 1, 12 denotes generally a replaceable filter cartridge comprising an elongate, generally transparent sleeve 14 made of plastic, glass, or the like, and containing intermediate its ends in crystalline form a conventional desiccant 15. This desiccant is of the type which is adapted to adsorb and/or absorb moisture, and upon doing so changes from one color to another, for example from pink to blue. These crystals are observable through the transparent wall of the sleeve 14.

Secured in each end of the sleeve 14 between the desiccant 15 and one of two disc-shaped membrane filters 16, which are seated coaxially over opposite ends of the sleeve 14, is a generally cylindrically shaped fibrous filter element 17. By way of example, element 17 may be made from non-woven Polyglas or the like. The disc-shaped filter elements 16 are secured snugly over opposite ends of the sleeve 14 by a pair of generally cup-shaped, transparent plastic end caps 19, which have externally flanged inner ends 20 that are sealingly secured by an epoxy resin or the like to the outer peripheral surface of sleeve 14. Integral with and projecting coaxially beyond the transverse outer end of each end cap 19 is a tapered, generally truncated-conical nozzle section 22, the inner end of which opens on the adjacent filter element 16 through a central opening 23 that is formed in the closed end of each end cap 19. Secured in the outer end of each nozzle section 22 is one end of one of a pair of conventional, barbed nipples 24, which are adapted releasably to connect the cartridge 12 to an instrument and to a supply of compressed air, respectively.

For example, as shown for the embodiment in FIG. 1, the upper nipple 24 is releasably connected to one end of a flexible tube or pipe T1, the opposite end of which is connected to a dental air syringe that is denoted generally by the letter S. This syringe S is of conventional design, and includes a manually-operable valve V for controlling the admission of compressed air from the cartridge 12 to the mouth of a patient. The other nipple 24, as shown in FIG. 1, is adapted to be connected by a flexible pipe or tube T2 to a supply of compressed air, which, preferably, has already been subjected to a primary air drying apparatus, such as for example the apparatus shown and described in the above-noted U.S. Pat. No. 3,279,151.

In use, the cartridge 12 is adapted to be releasably connected in the air line represented by the tubing T1, T2, and in such a position that it is located adjacent to the syringe S, so that during use the transparent sleeve 14 will be readily viewable or visible to the dentist or assistant who happens to be operating the syringe S. When first installed in the air line the desiccant 15 will have a primary distinguishing color, for example the color blue. However, if during use the air passing through the element or cartridge 12 contains any moisture, the latter will be absorbed by the desiccant 15, the color of which in turn will change progressively from, for example, blue to pink. This change in color signifies that moisture is being withdrawn from the air, and thus provides the dentist or other operator with a ready reference to determine whether or not the air entering the patient's mouth is in fact dry. As long as the desiccant 15 remains blue or nearly blue, the dentist can be assured that substantially no moisture remains in the air that is being admitted to the patient's mouth.

Whenever the desiccant 15 becomes pink throughout its length, as represented by the length of sleeve 14, it will require replacement. This can be done simply by removing the tubular sections T1, T2 from opposite ends of the cartridge or element 12, and replacing it with a new cartridge, the desiccant of which will be blue, thus indicating that it is ready to be used for extracting moisture from air before the latter is discharged from the syringe S. Again, this replacement cartridge 12 can be used until its desiccant turns from blue to pink. Since the end caps 19 are not removable from sleeve 14, the dentist may dispose of the used cartridge 12.

As noted above, the cartridge 12 of this first embodiment is particularly suited for use as a supplemental air dryer, and during use generally will not be required to remove particularly large quantities of moisture from the air that is supplied by the tube T2. Under normal conditions, therefore, the cartridge 12 can be repeatedly used before requiring replacement. Moreover, in view of the nature of the construction of this first embodiment, it will be apparent that the cartridge 12 will function properly regardless of the direction that the air travels through the cartridge. Also, in addition to the desiccant, the filter elements 16 and 17 assist in removing not only moisture and oil, but also any particulate matter from the compressed air prior to its discharge from the syringe S.

Referring now to the embodiment shown in FIG. 2, wherein like numerals are employed to denote elements similar to those shown in the first embodiment, 12' denotes a modified cartridge which is similar to that described in connection with FIG. 1, except that instead of filling the entire sleeve 14 with the desiccant 15, only part of the sleeve 14 is filled with the desiccant, and the remaining portion contains a generally cylindrically shaped oil filter element 25, which by way of example may be of the type sold by Deltech Engineering, Inc. of Century Park, New Castle, Del. as model 020. Prior to its use element 25 has a particular starting or basic color, for example pink, and is designed to filter out from the air passing through element 12' any oil which happens to be in the air. The oil collects on the surface of element 25 and tends progressively to change its color from pink to red, depending upon the amount of oil that it removes from the air. In the embodiment illustrated the upper end of element 25 is shown to be separated from the desiccant 15 by a perforated screen element 26, or the like.

Figure 2:
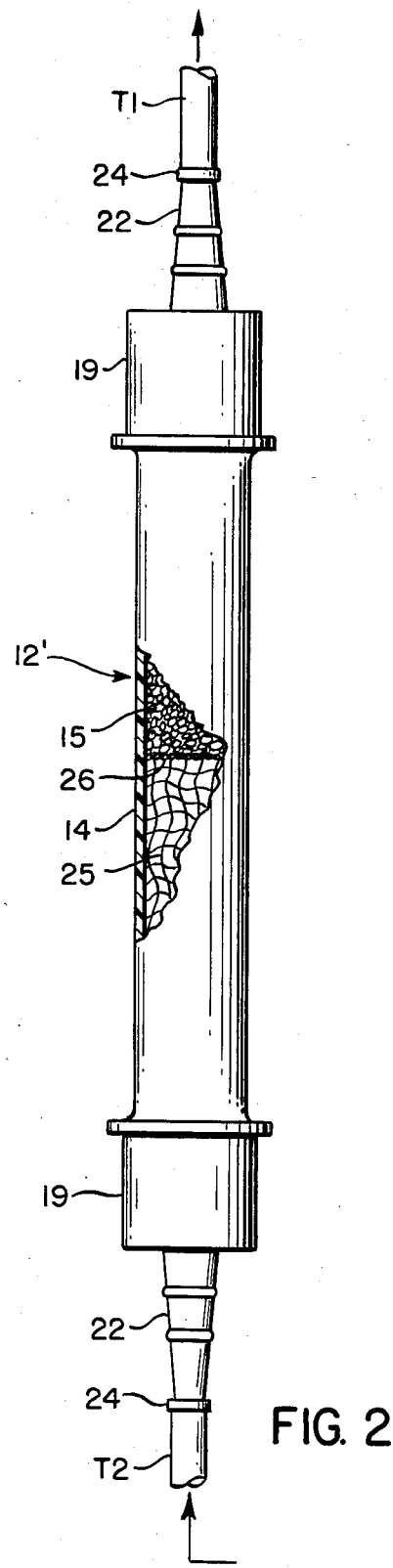
FIG. 2 is a fragmentary elevational view generally similar to FIG. 1, but illustrating a modified form of the filter cartridge, and excluding the illustration of the syringe.

The advantage of the embodiment shown in FIG. 2 is that it not only provides means for filtering out residual oil and water from the air that passes through cartridge 12', but it also functions to provide visible means for determining when the cartridge 12' will require replacement, depending upon when one or the other or both of the desiccant 15 and the element 25 have changed from their basic or starting colors to another color.

Although in the embodiment of FIG. 2 the desiccant 15 and filter element 25 are mounted in the same sleeve 14, it will be readily apparent that each could be mounted in separate sleeves. In such case, for example, two removable elements 12 and 12', one containing a desiccant 15 and the other an element 25, could be connected in series in the line represented by T1 and T2 so that one or the other could be replaced when and if necessary.

Figure 3:
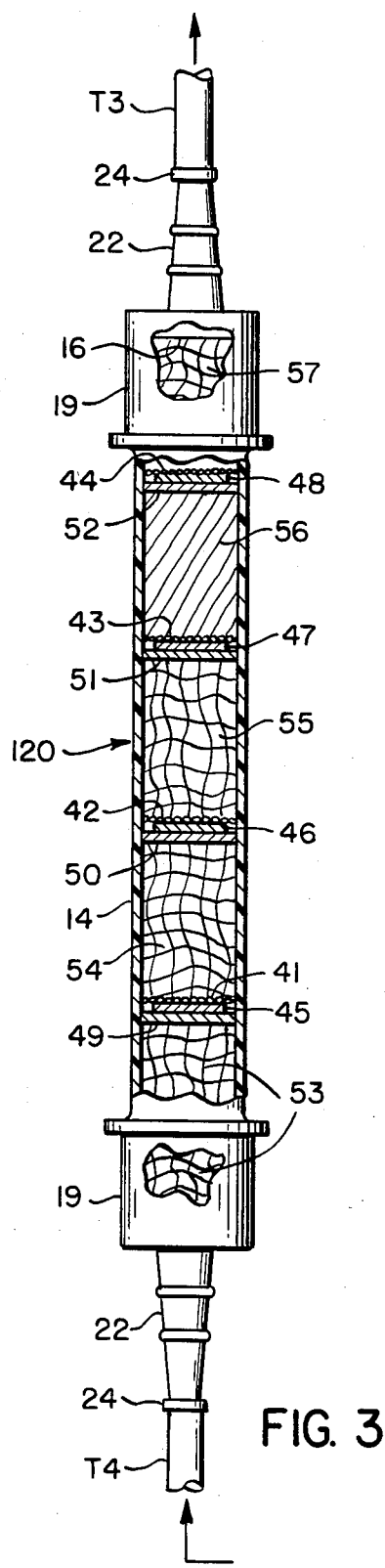
FIG. 3 is a view generally similar to FIG. 2 but illustrating still another form of the filter cartridge.

Referring now to FIG. 3, where like numerals again are employed to denote elements similar to those employed in the first embodiment, 120 denotes generally a modified filter cartridge which is particularly adapted to be connected in a dental syringe air line in series with one or more of the filter elements 12 and 12'. As in the case of the embodiments shown in FIGS. 1 and 2, cartridge 120 comprises a transparent sleeve 14, opposite ends of which are closed by the end caps 19, which in turn are connected by their associated nozzle sections 22 and fittings 24 with tubular sections T3 and T4 of the flexible air line which is adapted to supply compressed air to the syringe S.

Secured in the axial bore of the sleeve 14 of the cartridge 120, and extending transversely across the bore of the sleeve at axially spaced points therealong, are four, generally rigid screen members 41, 42, 43 and 44. Mounted in sleeve 14 to rest against the undersides of the screens 41-44 as illustrated in FIG. 3 are four, different, pressure-sensitive dye release capsules 45, 46, 47 and 48, respectively. Each of these capsules is held against the underside of the associated screen element 41, 42, 43 or 44 by one of four, different, generally disc-shaped membrane filters 49, 50, 51 and 52, which extend transversely across the bore in sleeve 14 to engage the undersides of the capsules 45, 46, 47 and 48, respectively. The three axial spaces formed in sleeve 14 beneath the filter elements 49, 50 and 51 are filled or packed with three different Microglas filtration elements 53, 54 and 55, respectively. The space in sleeve 14 beneath the filter element 52 and above screen 43 is filled with a membrane-type filtration element 56. The space above screen 44, and below the filter disc 16, which covers the upper end of sleeve 14, is filled with a Microglas filtration element 57. Cartridge 120 may otherwise be the same as cartridge 12.

The cartridge 120 is directional, in the sense that, when it is in use, compressed air should flow in the direction indicated by the arrows in FIG. 3, or in other words upwardly through the element 120 as shown in FIG. 3. The reason for this is that the various Microglas filtration elements and membrane filter discs in sleeve 14 are designed to remove progressively smaller particles from the air as it passes longitudinally through the cartridge 120. For this reason the various filter elements in cartridge 120 are designed so that the pores through which the air passes become progressively smaller as the air travels toward the upper end of the cartridge.

By way of example, the Microglas filtration materials forming the filter elements or wads 53, 54, 55 and 57 may be of the 10, 1.0, 0.4 and 0.2 milli-micron varieties, respectively. The associated membrane filter discs 49, 50, 51 and 52 likewise may be of the 10, 1.0, 0.4 and 0.2 milli-micron varieties, respectively. In such case the upper filter disc 16, which closes off the upper end of the sleeve 14, also will be of the 0.2 milli-micron variety. As a consequence, as air traverses upwardly through cartridge 120 the larger particles will be removed from the air adjacent the lower end of the cartridge 120 while the smaller particles will traverse upwardly through certain of the elements eventually to be removed by those elements having the smallest pore size—namely, elements 56, 52, 57, and the upper filter element 16.

In use, as the pores in each of the membrane filter discs 49, 50, 51 and 52 become progressively plugged or clogged by particles which they remove from the compressed air, a differential pressure develops across each disc. As these differential pressures increase, the respective membrane discs are caused to flex or shift axially upwardly in sleeve 14 in response to the increased back pressure. The discs 49, 50, 51 and 52, in turn, exert more and more axial pressure against the adjacent capsules 45, 46, 47 or 48, respectively, until such time that one or more of the capsules is caused to burst. Each of the capsules 45 through 48 contains a differently colored dye, and is designed also to rupture in response to a different predetermined bursting pressure. Whenever one or more of the capsules 45-48 bursts, its associated dye tends to bleed into, or to be absorbed by, the adjacent filter elements either above or below the respective capsule. In any case, as soon as the dye is released it tends rapidly to spread outwardly into the surrounding regions in the sleeve 14 thereby to provide a visual indication that the associated membrane filter has become unduly clogged, and thus indicating that the cartridge 120, or at least that particular membrane filter, should be replaced. This type of cartridge effectively monitors the presence of unwanted particles of different sizes, so that if clogging of a given membrane filter persists, it may indicate that the primary filtering apparatus is not functioning properly.

Obviously instead of incorporating a plurality of the membrane filters and associated dye release capsules in a given cartridge 120, it would be possible to utilize only a single membrane filter and capsule in the sleeve 14 of each of several different series - connected cartridges 120. This would permit the use of substantially smaller cartridges, and would obviate the need for replacing all four membrane filters 49-52 each time only one of them becomes clogged.

Normally dental air syringes of the type described are used in conjunction with compressors capable of generating an output pressure of approximately 100 lbs./sq.inch. This output is applied through a regulator which drops the pressure to approximately 42 lbs./sq. inch at the syringe S. The bursting pressures of the respective capsule 45-48 would therefore be selected to fall somewhere in a range of less than 42 lbs./sq. inch, depending upon the differential pressures which can be developed over the associated disc 49–52. Moreover, it will be understood also that although the above-described cartridges 12, 12' and 120 are particularly suited for insertion directly into the air line which supplies compressed air to the syringe S, it may be desirable, particularly when two or more such cartridges are employed, releasably to mount the cartridges on a stationary support located adjacent to the dental chair so that they will be readily observable by the dentist.

Figure 4:
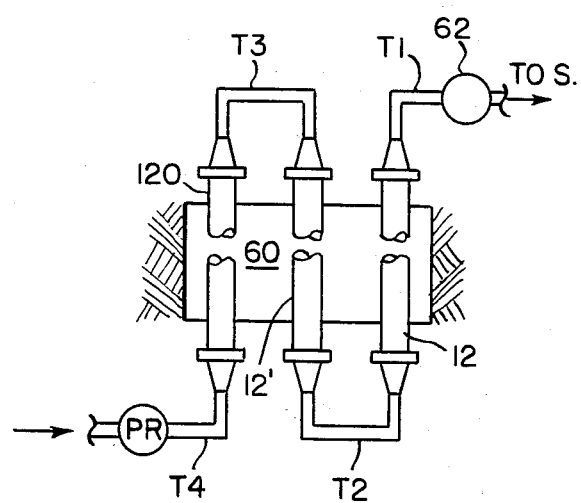
FIG. 4 is a diagramatic view illustrating one manner in which a plurality of filter cartridges made according to this invention are adapted to be connected in series with each other in the air supply line for a dental syringe.

As shown in FIG. 4, for example, the above-described cartridges 120, 12' and 12 could be releasable mounted on a stationary support 60 located adjacent a dental chair. The output of the associated compressor would then be supplied through a pressure regulator PR, the tubular conduit or line T4 to the cartridge 120, and from there through the tube section T3 to the filter cartridge 12', the output of which would pass through the tube section T2 and the cartridge 12 and section T1 to the syringe S. Also, if desired, a check valve 62 could be interposed between the section T1 of the line or tubing end of syringe S to prevent any reverse flow through the system.

From the foregoing it will be apparent that the present invention provides a relatively simple and inexpensive means for enabling a dentist visually to monitor the quality of the compressed air being delivered to a patient's mouth. The cartridges disclosed herein may be made from light, plastic materials so that they can be readily incorporated directly and removably in the existing flexible air supply lines currently in use by dentists, or alternatively, can be mounted on a stationary support immediately adjacent to a dental chair, in either case to be readily observable by the dentist. If desired, it will be apparent also that one or more of cartridges 12, 12' or 120 could include a granulated charcoal filter element, or the like, to remove undesirable odors from the compressed air.

Moreover, it will be apparent also that the barbed nipples 22 constitute only one conventional means of releasably connecting opposite ends of a cartridge in the compressed air line. Also, while the cartridges disclosed herein are particularly suitable for use by dentists, it will be readily apparent that they would be useful for any similar procedures requiring moisture and oil free compressed air supplies.

While this invention has been illustrated and described in connection with only certain embodiments thereof, it will be understood that it is capable of still further modification, and that this application is intended to cover any such modifications as may fall within the scope of one skilled in the art, or the appended claims.

I claim:

1. In combination with a hand-manipulable dental air syringe, a supply of compressed air having primary filtering means for removing undesirable matter from the compressed air, and a flexible air line for conveying compressed air from said primary filtering means to said syringe, the improvement comprising a disposable, non-replenishable filter cartridge removably connected in said flexible air line between said syringe and said primary filtering means and including
   a transparent sleeve,
   tubular means fixedly secured to opposite ends respectively, of said sleeve,
   said tubular means including coupling means releasably and sealingly connecting opposite ends of said sleeve in said flexible air line adjacent said syringe sot that said sleeve is viewable by the dentist manipulating said syringe, and so that compressed air from said primary filtering means will pass through said sleeve on its way to said syringe, and
   secondary filtering means mounted in said sleeve for removing residual undesirable matter from the compressed air,
   said secondary filtering means including a desiccant for removing residual moisture from the compressed air, said desicant being in direct contact with the inner peripheral surface of said sleeve and normally being of a first color when said cartridge is initally connected in said line, and being operative progressively to change to a second color as it removes moisture from said compressed air during use of the syringe.

2. The combination as defined in claim 1, wherein said secondary filtering means further includes a filter element for removing residual oil from said compressed air.

3. The combination as defined in claim 1, wherein said secondary filtering means further includes a porous membrane filter for removing residual particulate matter from said compressed air.

4. The combination as defined in claim 3, including
   a rupturable capsule secured in said sleeve adjacent to and downstream of said membrane filter relative to the direction of flow of compressed air through said sleeve,
   said capsule containing a dye of predetermined color, and disposed to be ruptured by said membrane filter in response to a predetermined back pressure created by the compressed air in said sleeve as said membrane filter becomes clogged during use.

5. The combination as defined in claim 4, wherein
   a plurality of said capsules and membrane filters are mounted in said sleeve with said capsules being secured in axially spaced relation to each other and each being positioned downstream and immediately adjacent to a different one of said membrane filters, and
   each of said capsules containing a different color dye.

6. The combination as defined in claim 5, wherein the pore diameters of successive ones of said membrane filters are progressively smaller, with the membrane filter having the largest pore diameter located adjacent the compressed air inlet end of said sleeve, and the membrane filter having the smallest pore diameter being located adjacent the compressed air outlet end of said sleeve.

7. The combination as defined in claim 6, wherein non-woven fibrous filter elements are mounted in said sleeve in the spaces between said axially spaced capsules.

8. The combination as defined in 6, wherein said membrane filters range in pore size from approximately 10 milli micron to 0.2 milli micron.

9. A disposable filter cartridge for removing residual contaminates from compressed air passed through a flexible air line from a filtered supply of compressed air to a hand manipulable air syringe, comprising
   an elongate housing open at opposite ends thereof,
   a pair of caps fixed over and closing opposite ends of said housing, each of said caps having therethrough an axial bore communicating with the interior of said housing, a pair of porous membrane filter elements mounted in said caps and overlying opposite ends, respectively, of said housing, tubular means integral with and projecting from each of said caps for releasably connecting the interior of said housing in a compressed air supply line for an air syringe, whereby compressed air will be caused to travel longitudinally through said housing and said pair of filter elements during use of said syringe, and a desiccant mounted in said housing between said membrane filter elements and operative to remove moisture from the air passing through said housing, and operative progressively to change from a first to a second color at a rate proportionate to the amount of the moisture removed thereby from said air, at least a portion of said housing intermediate its ends being transparent, whereby any change in the color of said desiccant will be readily observable from the exterior of said housing.

10. A filter cartridge as defined in claim 9 including a further filter element mounted in said housing adjacent said desiccant and normally having a color different from the normal color of said desiccant, and said further filter element being disposed to remove oil from said air passing through said housing, and progressively to change from said normal color thereof to another color in response to the quantity of oil it removes from said air.

11. A filter cartridge as defined in claim 9, including a third, porous filter element mounted in said housing for limited movement between opposite ends thereof, and a rupturable capsule mounted in said housing adjacent to and downstream of said third element to be engaged and ruptured thereby when said third element becomes clogged and is forced axially against said capsule by the back-pressure created by said compressed air, said capsule containing a dye which is released and is viewable through said transparent portion of said housing when the capsule is ruptured.

* * * * *